United States Patent
Manwaring et al.

(10) Patent No.: US 7,833,165 B2
(45) Date of Patent: Nov. 16, 2010

(54) SYSTEM FOR MONITORING NEURAL SHUNT FUNCTION AND ASSOCIATED METHODS

(76) Inventors: Kim Manwaring, 1915 E. Muirwood Dr., Phoenix, AZ (US) 85048; Preston Manwaring, 54 Buckingham Pl., Lebanon, NH (US) 03766; Mark Manwaring, 1270 E. 370 South, Payson, UT (US) 84651

( * ) Notice: Subject to any disclaimer, the term of this patent is extended or adjusted under 35 U.S.C. 154(b) by 3 days.

(21) Appl. No.: 12/064,002

(22) PCT Filed: Aug. 15, 2006

(86) PCT No.: PCT/US2006/032013
§ 371 (c)(1),
(2), (4) Date: Jul. 31, 2008

(87) PCT Pub. No.: WO2007/022288
PCT Pub. Date: Feb. 22, 2007

(65) Prior Publication Data
US 2008/0319340 A1    Dec. 25, 2008

(51) Int. Cl.
*A61B 5/00*  (2006.01)
*A61B 5/02*  (2006.01)

(52) U.S. Cl. ............ 600/486; 600/485; 600/500; 600/561

(58) Field of Classification Search ............ 604/8–9; 600/561, 485, 486, 500
See application file for complete search history.

(56) References Cited

U.S. PATENT DOCUMENTS

| | | | |
|---|---|---|---|
| 5,101,828 A * | 4/1992 | Welkowitz et al. | 600/481 |
| 5,353,800 A * | 10/1994 | Pohndorf et al. | 600/486 |
| 5,527,822 A | 6/1996 | Scheiner | |
| 5,795,307 A * | 8/1998 | Krueger | 600/561 |
| 5,997,484 A | 12/1999 | Sugahara | |
| 6,193,669 B1 * | 2/2001 | Degany et al. | 600/486 |
| 6,354,999 B1 * | 3/2002 | Dgany et al. | 600/486 |
| 6,585,677 B2 * | 7/2003 | Cowan et al. | 604/9 |
| 6,589,189 B2 * | 7/2003 | Meyerson et al. | 600/561 |
| 7,403,805 B2 * | 7/2008 | Abreu | 600/318 |
| 2002/0183628 A1 * | 12/2002 | Reich et al. | 600/486 |
| 2004/0087863 A1 * | 5/2004 | Eide | 600/500 |
| 2004/0260229 A1 * | 12/2004 | Meir | 604/9 |
| 2005/0119602 A1 | 6/2005 | Murphy et al. | |

* cited by examiner

*Primary Examiner*—Patricia C Mallari
(74) *Attorney, Agent, or Firm*—Thorpe North & Western LLP

(57) ABSTRACT

A system and method for evaluating neural shunt functionality is provided. Accordingly, in one aspect a method for monitoring neural shunt functionality may include measuring a first intracranial pressure pulse inside the shunt, measuring a second intracranial pressure pulse outside the shunt, and comparing pulsatile characteristics from the first measurement to the second measurement in order to determine shunt functionality.

10 Claims, 3 Drawing Sheets

SYSTEM FOR MONITORING NEURAL SHUNT FUNCTION AND ASSOCIATED METHODS

FIELD OF THE INVENTION

The present invention relates to methods and systems for monitoring the patency of neural shunts. Accordingly, this invention involves the fields of neurology, medicine and other health sciences.

BACKGROUND OF THE INVENTION

The monitoring of intracranial pressure is important in the management of head trauma and many neural disorders. Edema associated with many pathologic conditions of the brain may cause an increase in intracranial pressure that may in turn lead to secondary neurological damage. In addition to head trauma, various neurological disorders may also lead to increased intracranial pressure. Examples of such disorders may include intracerebral hematoma, subarachnoid hemorage, hydrocephalic disorders, infections of the central nervous system, and various lesions to name a few.

As a specific example, hydrocephalus is characterized by increased intracranial pressure due to an excess of cerebrospinal fluid, which is often the result of malabsorption or impediment of clearance in the intraventricular space within the brain or subarachnoid spaces about the brain. Hydrocephalus is often treated by insertion of a diverting catheter into the ventricles of the brain or into the lumbar cistern. Such a catheter or shunt is connected by a regulating valve to a distal catheter which shunts the spinal fluid to another space where it can be reabsorbed. Examples of common diversion sites include the peritoneum of the abdomen via a ventriculoperitoneal shunt or lumboperitoneal shunt or the atrium of the heart via a ventriculoatrial shunt. Although the symptoms of excessive intracranial pressure and associated ventricular enlargement may be relieved by this procedure, it is not uncommon for the shunt apparatus to become obstructed, resulting in shunt failure. An invasive surgery known as shunt revision may be performed to replace or repair the failed shunt. While shunts may become obstructed at a valve or distal tubing level, a great majority of shunt failures are due to proximal obstruction at the tip of the proximal catheter due to gradual growth of scar about the catheter tip or ingrowth of tissue such as choroid plexus into the catheter tip. A wide variety of techniques of positioning of the catheter and various designs have been explored to diminish obstruction, including many modifications of the side inlet holes of the proximal catheter tip. These have met with modest success at best. The routine clinical approach to shunt failure is therefore to replace the obstructed component and to employ higher pressure regulating valves or related valve components to diminish the tendency of overshunting, a condition characterized by the ventricles eventually becoming much smaller than normal and hugging the proximal catheter.

It is not always readily apparent to a clinician that a shunt has failed when a patient having a shunt exhibits early shunt failure symptoms such as headache and nausea. Various techniques have been employed to determine functionality of the shunt. For example, an imaging test of the brain such as CT scan, MRI scan, or ultrasound may show progressive ventricular enlargement compared to previous scans. As another example, shunt failure may be demonstrated by inserting a needle into the shunt valve reservoir and attempting to aspirate. An inability to do so may indicate a failed shunt, however a working shunt in very small or slit-like ventricles may act similarly, thus incorrectly reporting that the shunt has failed. As a further example, flow studies such as radioisotope, ultrasound or MRI may show minimal or no flow. Also, a previously implanted intracranial pressure sensor may provide evidence that the shunt has failed or is failing.

The various shunt functionality tests previously utilized may not be preferred in many circumstances due to a high degree of inaccurate results or due to an unnecessary level of invasiveness. As such, systems and methods for improvement in the accuracy of shunt failure detection due to proximal obstruction, guidance to physicians of the degree of patency of the neural shunt device, and simplified determination of restoration of shunt functionality would impact the management of hydrocephalus and other neural disorders and head trauma.

SUMMARY OF THE INVENTION

Accordingly, the present invention provides systems and methods for monitoring neural shunts in order to provide physicians and other health workers with information pertaining to patency, and thus improve the health and/or the prognosis of individuals having neural shunts. In one aspect, for example, a method for monitoring neural shunt functionality is provided. Such a method may include measuring a first intracranial pressure pulse inside the shunt, measuring a second intracranial pressure pulse outside the shunt, and comparing pulsatile characteristics from the first measurement to the second measurement in order to determine shunt functionality.

Various methods of measuring the first intracranial pressure pulse inside the shunt are contemplated, and it should be understood that any such method for obtaining such a measurement is considered to be within the scope of the present invention. In one aspect, for example, measuring inside the shunt may be accomplished by inserting a pressure sensor into the shunt to measure the first intracranial pressure pulse. Inserting the pressure sensor into the shunt may include insertions into the shunt itself and into those structures that are fluidically coupled to the shunt.

Various methods of measuring the second intracranial pressure pulse outside the shunt are contemplated, and it should be understood that any such method for obtaining such a measurement is considered to be within the scope of the present invention. Measurements of the second intracranial pressure pulse may be obtained from a location inside the cranium or from a location outside the cranium. In one aspect, for example, measuring from a location outside the cranium may include measuring the second intracranial pressure pulse from tympanic membrane displacements. In another aspect, measuring from a location outside the cranium may include measuring the second intracranial pressure pulse from a supraorbital artery.

The comparison of the pulsatile characteristics from the first measurement to the pulsatile characteristics from the second measurement may allow the level of functionality of the neural shunt to be determined. Various pulsatile characteristics may be utilized to determine shunt functionality. In one aspect, the pulsatile characteristics may include pulse amplitude. In another aspect, the pulsatile characteristics may include a characteristic of the pulse waveform such as pulse risetime or pulse falltime. Additionally, numerous methods of comparing pulsatile characteristics are possible. One such method may include a determination of correlation between the first intracranial pressure pulse and the second intracranial pressure pulse.

In another aspect, the present invention provides a system for monitoring neural shunt functionality. Such a system may include a first sensor configured to measure a first intracranial pressure pulse from inside the shunt and a second sensor configured to measure a second intracranial pressure pulse from outside the shunt. The system may further include a computational device functionally coupled to the first sensor and to the second sensor that is capable of comparing pulsatile characteristics between the first intracranial pressure pulse and the second intracranial pressure pulse.

The first sensor may be configured to measure the first intracranial pulse from a variety of locations inside the shunt. Inside the shunt is intended to include locations or structures that are in the shunt itself and locations or structures that are fluidically coupled to the shunt. Examples of such locations or structures that are fluidically coupled may include, without limitation, shunt tubing, tapping reservoirs such as a Rickham reservoir, etc. Additionally, the first sensor may include a variety of configurations to accomplish such a measurement. In one aspect, however, the first sensor may include a hollow needle coupled to a pressure sensor.

The second sensor may be configured to measure the second intracranial pressure pulse from a variety of locations. It should be understood that any method or location for measuring the second intracranial pressure pulse from outside of the shunt would be considered to be within the present scope. In one aspect, the arterial pulsation may be measured from within the cranium from an implanted device such as a pressure sensor. In another aspect, the second intracranial pressure pulse may be measured from outside the cranium. Examples of such extracranial measurement may include, without limitation, measurements from a supraorbital artery, tympanic membrane displacements, retinal tissue, etc.

In another aspect of the present invention, the first sensor may further be associated with an access port configured to allow access of a medical instrument to the shunt. In one aspect, the medical instruments utilized in the access port may be used to clear an occluded portion of the neural shunt. Various medical instruments are contemplated, and may include, without limitation, radiofrequency probes, laser probes, etc.

DETAILED DESCRIPTION

Definitions

Figure 1:
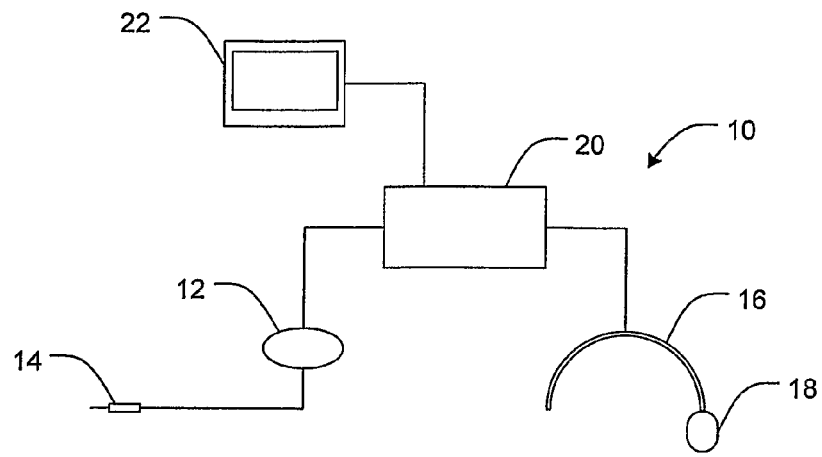
FIG. 1 is a schematic view of a system for determining neural shunt functionality according to an embodiment of the present invention.

In describing and claiming the present invention, the following terminology will be used in accordance with the definitions set forth below.

The singular forms "a," "an," and, "the" include plural referents unless the context clearly dictates otherwise. Thus, for example, reference to "a shunt" includes reference to one or more of such shunts, and reference to "an artery" includes reference to one or more of such arteries.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals.

As used herein, the term "normal" as it relates subjects refers to intracranial pressure or brain compliance levels in a subject that would be determined by one of ordinary skill in the art to not require medical treatment.

As used herein, the term "abnormal" as it relates subjects refers to intracranial pressure or brain compliance levels in a subject that would be determined by one of ordinary skill in the art to require medical treatment, though such medical treatment may not be immediately required.

As used herein, the term "intracranial pressure pulse" refers to a pressure pulsation pattern or, in other words, pressure fluctuations of a pulsatile nature that originate from the arterial pulsations of the heart.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range.

Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The Invention

As has been described, the various neural shunt functionality tests previously utilized may not be preferred in many circumstances due to a high degree of inaccurate results or due to an unnecessary level of invasiveness. Accordingly, the present inventors have discovered a way of accurately determining the patency or functionality of the shunt of a subject with minimal invasiveness. Generally, intracranial pressure measured inside the shunt may be compared to intracranial pressure measured outside the shunt to determine shunt patency. More specifically, pulsatile characteristics of an intracranial pressure pulse measured outside the shunt can be compared to pulsatile characteristics of an intracranial pressure pulse measured from inside the shunt to determine patency. As openings in the shunt between the shunt lumen and the intracranial environment become occluded, pressure within the shunt drops and pulses from the arterial flow become attenuated. Little if any pulsatile pressure can be measured from within a non-functional shunt. Thus, shunt patency may be determined by comparing pulsatile characteristics of arterial pressure pulsations measured in the shunt lumen to the pulsatile characteristics of arterial pressure pulsations from the intracranial environment. Once the patency of the shunt is determined, replacement or repair of the device can be accomplished. Such a "real-time" determination of shunt functionality may allow medical professionals to re-open occluded portions of the shunt by percutaneous removal of obstructive debris while observing shunt patency to ensure success of the procedure.

Accordingly, various aspects of the present invention provide methods for monitoring neural shunt functionality whereby intracranial pressure is measured both inside and outside the shunt, and such measurements are compared to determine shunt patency. Various non-limiting methods of measuring intracranial pressure in these locations are described below.

Numerous neural shunts are known to those of ordinary skill in the art. As such, no limitations are intended by the neural shunt configurations described herein, which are intended to be merely exemplary. A ventriculoperitoneal shunt, for example, may typically a proximal catheter which is inserted into a cerebral ventricle coupled to a distal catheter that delivers spinal fluid to a distal site for reabsorption by the body, such as the peritoneal cavity of the abdomen. The proximal catheter may be a silicone tube with a closed tip, but may include a multiplicity of small side holes in rows at the tip to allow cerebrospinal fluid (CSF) to enter into the shunt. In many inserted shunts, these holes become gradually occluded over time as a result of scarring due to adjacency of the ependymal wall of the ventricle or due to ingrowth of choroid plexus. When the last hole with access into the lumen of the catheter becomes obstructed, the shunt fails and is no longer able to convey CSF. In such a situation, symptoms of increasing intracranial pressure result.

Various other structures may also be present in a typical ventriculoperitoneal shunt. For example, a tapping reservoir, often also known as a Rickham reservoir, may be fluidically coupled between the proximal and distal catheters to allow percutaneous sampling of CSF to determine, among other things, infection. Additionally, a pressure regulating valve is often fluidically coupled between the catheters distal to the tapping reservoir. This valve regulates the flow of CSF from the ventricle in order to maintain normal ventricular CSF levels. The reservoir may be tapped by a needle and connected to a manometer to determine an approximate intracranial pressure, so long as the pressure does not exceed the regulating valve's opening pressure. The CSF column within the manometer oscillates as a result of the systolic and diastolic shifts due to pulsation of intracranial pressure. However, such oscillation may be minimally, if at all, demonstrated in patients where the proximal catheter is nearly obstructed. Further, if the proximal catheter is fully obstructed due to scarring or ingrowth of the side holes, CSF will not displace into the manometer and little if any CSF may be aspiratable by application of a syringe with negative pressure to the needle. When the catheter is partially patent or the ventricles are collapsed around a patent catheter, equivocal or misleading results may be observed.

As has been described, intracranial pressure measurements may be obtained from the shunt lumen by percutaneously inserting a pressure sensor or transducer into the shunt. Such insertion may occur via the tapping reservoir, the proximal catheter, the distal catheter, or any other structure of the shunt or structure that is fluidically coupled to the shunt whereby access may be provided. In one aspect, a needle coupled to a pressure sensor may be percutaneously inserted into the tapping reservoir to obtain intracranial pressure measurements from within the shunt. As has been described, intracranial pressure can be measured in the oscillations of intracranial pulsation due to arterial pulsations. These intracranial pressure pulses may be measured from within a functional neural shunt. It should be noted that any location within the shunt where intracranial pressure pulses may be measured is within scope of the present invention, and would include those locations that are intracranial and those that are extracranial.

As has been described, intracranial pressure pulsation measured outside of the shunt may be compared to intracranial pressure pulsation measured inside the shunt to assess shunt functionality. Various measurement locations for the extrashunt arterial pulsations are contemplated. It should be noted, however, that any measurement location where intracranial pulsation pressure can be determined outside the shunt would be considered to be within the scope of the present invention. In some aspects, for example, the intracranial pressure pulses can be measured from within the cranium. Such measurements may be obtained from, for example, previously implanted pressure sensors that are external to the shunt.

In other aspects, the intracranial pressure pulses can be measured from a location that is outside of the cranium. Because measurements taken from outside the cranium are often noninvasive they may often be preferable in many cases. Any location from which intracranial pressure pulses can be measured should be considered to be within the scope of the present invention. In one aspect intracranial pressure pulses may be measured from the supraorbital artery, derived from the internal carotid artery. The intracranial internal carotid artery bifurcates into two branches, one of which is the ophthalmic artery. This artery exits the intracranial space to become the supraorbital artery, which passes over the forehead through the supraorbital foramen and above the ocular globe. Intracranial arterial pulsations are altered by intracranial pressure and brain compliance or stiffness, and such alterations in waveform are manifest downstream in the course of the supraorbital artery where it exits into the plane beneath the scalp. Thus the supraorbital artery may provide a measurement of intracranial pressure pulses through measurement at the forehead of the subject that can be compared with measurements obtained in the shunt lumen.

In another aspect, intracranial pressure pulses may be measured by detection of tympanic membrane displacement, a pulsatile pattern corresponding to the intracranial arterial pulsation. Such measurement may occur by, for example, placing a tympanic membrane displacement sensor into the external ear canal of one ear of the subject. Intracranial pulsation is thus transmitted through the middle ear bones to the tympanum, and thus to the sensor located in the external ear canal. These intracranial pulsations can be compared to the measurements in the shunt lumen to determine shunt functionality.

Other methods of measuring intracranial pressure pulses may also be utilized, such as, without limitation, measurements from retinal tissue, measurements from MRI or other neural imaging devices, ultrasound, etc.

Various devices are contemplated for the measurement of intracranial pressure pulses. It should be noted that any device capable of measuring such an intracranial pressure pulse should be considered to be within the scope of the present invention. Examples may include, without limitation, pressure transducers, displacement sensors, impedance sensors, voltage sensors, and combinations thereof.

FIG. 1 shows one example of a system 10 for monitoring neural shunt functionality according to aspects of the present invention. Such a system 10 may include a pressure transducer 12 functionally coupled to a needle 14 for percutaneously accessing a neural shunt. A tympanic membrane displacement sensor 16 having at least one piezoelectric sensor 18 is configured to couple in an airtight fashion to the external ear canal to transduce displacement of the tympanic membrane. The waveform derived from such a tympanic membrane displacement sensor 16 is very similar in pulsatile shape to a waveform derived from an implanted pressure sensor in the brain. The voltage output from the pressure transducer 12 and the piezoelectric sensor 18 may be amplified and transduced by an analog to digital converter associated with a computational device 20. In one aspect, the resulting waveforms may be displayed on a display device 22 that is functionally coupled to the computational device 20.

In one aspect, displacement of the tympanic membrane may be derived from a conventional stethoscope. Specifically, a conventional stethoscope ear set may be modified such that a piezoelectric sensor is substituted for the bell of the stethoscope. Pressure fluctuations in the tympanic membrane are transmitted through the ear set of the stethoscope to produce voltage oscillations in the piezoelectric sensor. This design may be readily adapted to patients of all ages due to the spring of the stethoscope that allows the snug fit of earplugs simultaneously and under equal pressure into both ear canals.

The comparison of pulsatile characteristics of intracranial arterial flow measured within a shunt and intracranial arterial flow measured outside the shunt may provide an accurate measurement of the functionality of the shunt. Various pulsatile characteristics may be utilized to provide a determination of shunt patency. Examples include, without limitation, pulse amplitude, pulse risetime, pulse fall time, etc. In considering pulse amplitude, for example, as the functionality of a shunt decreases do to occlusion, the amplitude of the intracranial pressure pulses within the shunt will proportionally decrease. As such, a comparison of the amplitude of pulses derived from intracranial arterial pulsation outside of the shunt to the amplitude of pulses derived from intracranial arterial pulsation inside the shunt may provide an accurate measure of the functionality of the shunt. Any method of comparing the pulsatile characteristics of the measured intracranial arterial pulsation should be considered within the present scope. In one aspect, correlation between the waveforms may be a useful comparison technique.

EXAMPLES

The following examples are provided to promote a more clear understanding of certain embodiments of the present invention, and are in no way meant as a limitation thereon.

Example 1

Figure 2:
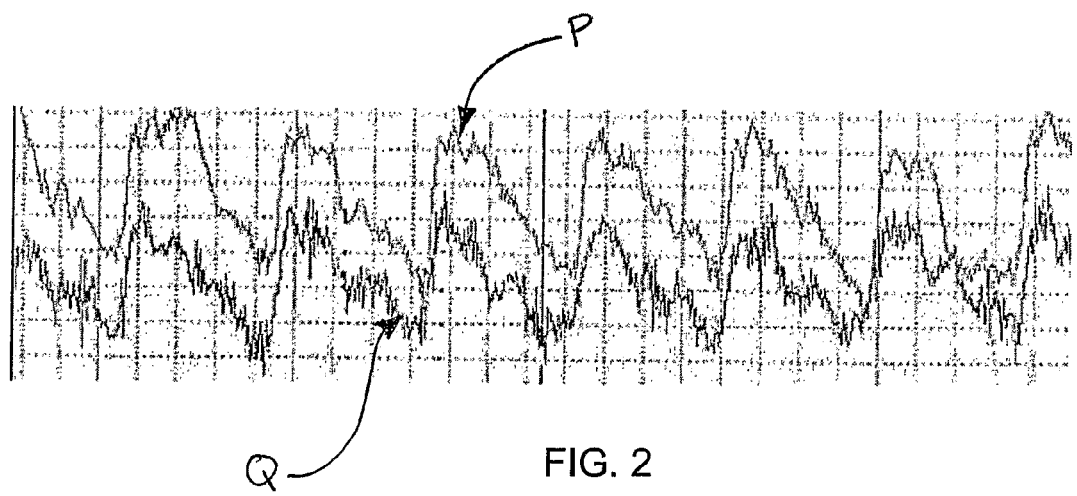
FIG. 2 is a representation of pulsatile waveforms according to another embodiment of the present invention.

FIG. 2 shows voltage waveforms P and Q from a subject. Waveform P is derived from a pressure sensor coupled to a percutaneous needle that has been passed into a tappable reservoir of a neural shunt. Waveform P represents the intracranial pressure coupled through the proximal catheter from the lateral ventricle. Waveform Q is derived from a tympanic membrane displacement sensor. Very similar waveform shapes are recorded in both traces. If the proximal catheter were partially blocked, waveform P would be diminished in amplitude, lack detail for harmonics, and would be slightly delayed compared to the tympanic membrane displacement waveform Q. Accordingly, shunt patency may be determined by comparing intracranial pressure pulsation waveforms from within the shunt to those from outside the shunt.

Figure 3:
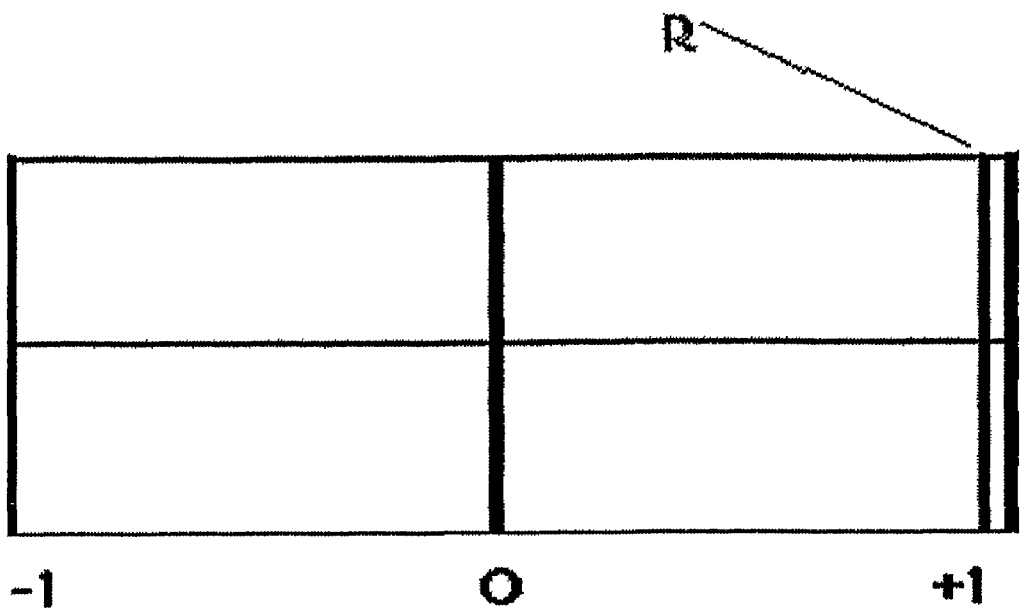
FIG. 3 is a correlation relationship of pulsatile waveforms according to yet another embodiment of the present invention.
Figure 4:
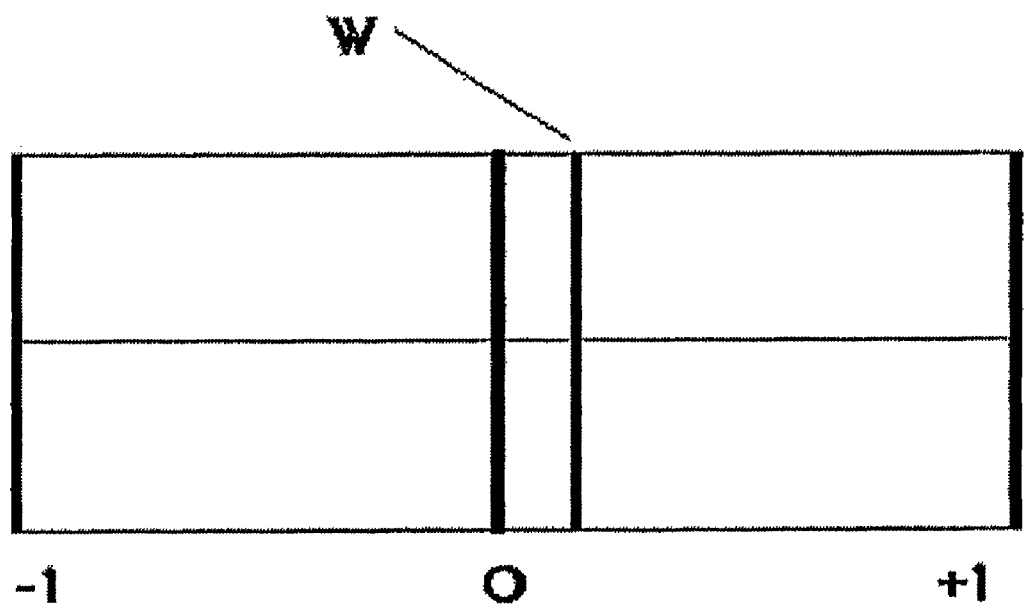
FIG. 4 is a correlation relationship of pulsatile waveforms according to a further embodiment of the present invention.

A correlation graph is provided in FIG. 3 derived from real time feedback of the similarities between the waveforms P and Q. To derive such a real time correlation, voltages from waveforms P and Q are normalized to an equivalent amplitude. The amplitude of each waveform channel is fed into a stereo phase shifter oscillating at 150 Hz to align the phase of each of the waveforms. Waveforms P and Q shift phase identically and thus remain in phase with each other. The two waveform channels are then fed into a stereo sound card and the correlation is continuously derived by audio software. Identical waveforms in phase yield a correlation of +1. If the proximal catheter is partially blocked, the waveform P will be diminished in amplitude, deficient in harmonic detail, and slightly phase delayed. As the blockage increases, the correlation diminishes toward zero. In FIG. 3, the correlation marked at R is close to +1, indicating a good correlation between the waveforms. If no waveform is derived from percutaneous puncture transduction of the pressure from the shunt, all holes in the proximal catheter are occluded by either ingrowth, scarring, or isolation from a hugging slit ventricle. As an example, FIG. 4 shows the correlation of waveforms P and Q in a proximal catheter of a subject with only one hole functioning. In this case, the correlation marked at W is close to 0, indicating poor correlation between the waveforms.

Figure 5:
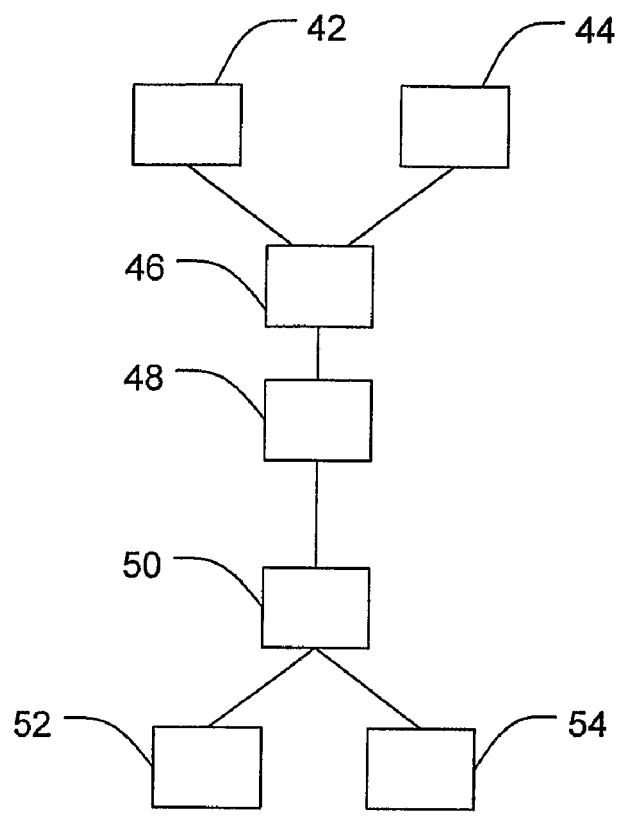
FIG. 5 is a block diagram according to yet a further embodiment of the present invention.

FIG. 5 is a block diagram showing one method of deriving the correlation coefficient. Waveforms P and Q are measured by transducers 42 and 44. The waveforms are equalized in amplitude by an amplitude equalizer 46. Equalized waveforms are phase shifted at 150 Hz by a phase shifter 48. These phase shifted waveforms are fed to a computer stereo sound card 50 and analyzed by software to derive a correlation coefficient. The real-time waveforms 52 may be displayed along with the correlation 54. To simplify the surgical environment, phase shifted data at 150 Hz may be transmitted wirelessly by conventional transmitter and receiver combinations to the computer display.

Example 2

A percutaneous device is utilized for the re-opening of an obstructed proximal catheter. Percutaneous access into a Rickham reservoir with an 18 gauge Teflon IV and needle combination is accomplished via a side port adaptor (Tuohy-Borst adaptor, Codman and Shurtleff, Raynham, Mass.) coupled to the shunt. The in-line access point of the adaptor allows passage of a radiofrequency probe (Codman ME-2 Microendoscopic electrode, Codman and Shurtleff) through the Rickham reservoir to the tip of the proximal catheter where side holes are occluded. The proximal catheter is re-opened by using a conventional radiofrequency surgical generator employing the coagulation waveform at approximately 25 watts. When the occluded holes are re-opened, waveform P immediately re-appears and the correlation co-efficient recovers steadily from zero to near one, giving the clinician immediate feedback of success of restoration. The percutaneous access combination of needle and electrode are then removed.

Figure 6:
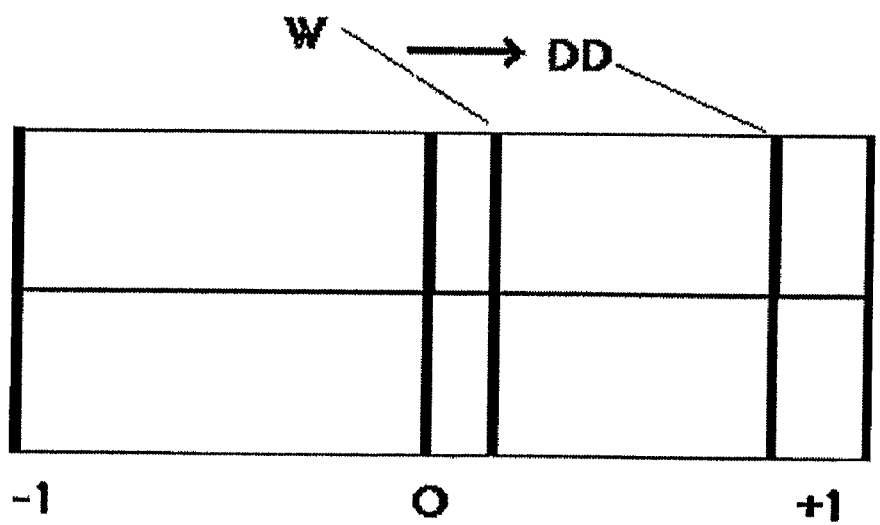
FIG. 6 is correlation relationship of pulsatile waveforms according to another embodiment of the present invention.

FIG. 6 is a correlation coefficient graph showing the obstructed state of a neural shunt (W) followed by nearly full recovery (DD) of equivalency of waveforms P and Q following removal of occlusive debris in proximal catheter B. It will be apparent to the clinician that recovery of CSF oscillation and flow as seen visually by moving CSF or air bubbles in the transparent adaptor is a good indicator of restored patency. However, the improved quantification of restoration of an open proximal catheter by derivation of the correlation between waveforms P and Q significantly strengthens that insight and often prompts further efforts at debris removal.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for monitoring neural shunt functionality, comprising:
   measuring a first intracranial pressure pulse inside the shunt using a first sensor;
   measuring a second intracranial pressure pulse outside the shunt using a second sensor; and
   comparing pulsatile characteristics from the first measurement to the second measurement using a computational device in order to determine shunt functionality.

2. The method of claim 1, wherein measuring inside the shunt further includes inserting the first sensor into the shunt to measure the first intracranial pressure pulse.

3. The method of claim 2, wherein inserting the first sensor into the shunt further includes inserting the first sensor into a structure that is fluidically coupled to the shunt.

4. The method of claim 1, wherein measuring outside the shunt further includes measuring the second intracranial pressure pulse from a location outside the cranium.

5. The method of claim 4, wherein measuring from a location outside the cranium includes measuring the second intracranial pressure pulse from tympanic membrane displacements.

6. The method of claim 4, wherein measuring from a location outside the cranium includes measuring the second intracranial pressure pulse from a supraorbital artery.

7. The method of claim 1, wherein the pulsatile characteristics include pulse amplitude.

8. The method of claim 1, wherein the pulsatile characteristics include pulse risetime or pulse falltime.

9. The method of claim 1, wherein comparing pulsatile characteristics further includes determining a correlation measurement between the first intracranial pressure pulse and the second intracranial pressure pulse.

10. The method of claim 1, further comprising clearing an occluded portion of the neural shunt.

* * * * *